US012350402B2

(12) United States Patent
Kim

(10) Patent No.: US 12,350,402 B2
(45) Date of Patent: Jul. 8, 2025

(54) COMPOSITE, MANUFACTURING METHOD THEREFOR, AND COSMETIC SURGERY FILLER COMPOSITION USING SAME

(71) Applicant: VAIM Co., Ltd., Daejeon (KR)

(72) Inventor: Gun Poong Kim, Chungcheongbuk-do (KR)

(73) Assignee: VAIM Co., Ltd., Daejeon (KR)

( * ) Notice: Subject to any disclaimer, the term of this patent is extended or adjusted under 35 U.S.C. 154(b) by 0 days.

(21) Appl. No.: 18/575,043

(22) PCT Filed: Jun. 14, 2023

(86) PCT No.: PCT/KR2023/008194
§ 371 (c)(1),
(2) Date: Dec. 28, 2023

(87) PCT Pub. No.: WO2023/244011
PCT Pub. Date: Dec. 21, 2023

(65) Prior Publication Data

US 2024/0261473 A1    Aug. 8, 2024

(30) Foreign Application Priority Data

Jun. 14, 2022 (KR) .................. 10-2022-0072130

(51) Int. Cl.
*A61K 47/28* (2006.01)
*A61L 27/36* (2006.01)
*A61L 27/48* (2006.01)
*A61L 27/58* (2006.01)

(52) U.S. Cl.
CPC .......... *A61L 27/48* (2013.01); *A61L 27/3691* (2013.01); *A61L 27/58* (2013.01); *A61L 2400/06* (2013.01); *A61L 2430/34* (2013.01)

(58) Field of Classification Search
CPC ..... A61K 27/48; A61K 27/58; A61L 2400/06; A61L 2430/34; A61L 27/3691; C08L 67/04
See application file for complete search history.

(56) References Cited

U.S. PATENT DOCUMENTS 10,765,753 B2    9/2020   Lee et al.

FOREIGN PATENT DOCUMENTS

| EP | 3730161 A1 | * | 10/2020 |
| KR | 10-1725279 B1 | * | 4/2017 |
| KR | 10-2017-0123099 A | | 11/2017 |
| KR | 10-1801566 B1 | | 11/2017 |
| KR | 10-1831079 B1 | | 2/2018 |

(Continued)

OTHER PUBLICATIONS

PLA, Research on Improving the PLA Microparticle manufacturing Process, Final Report on Product Process Improvement Technology Develpement Project, VAIM Co. Limited, pp. 1-35. (Year: 2015).*

(Continued)

*Primary Examiner* — Carlos A Azpuru
(74) *Attorney, Agent, or Firm* — Sughrue Mion, PLLC

(57) ABSTRACT

The present invention relates to a composite, a manufacturing method therefor, and a cosmetic filler composition using same, the composite comprising biodegradable particles with a network structure therein, and a water-soluble polymer. The composite has a cake formulation, and thus has excellent long-term storability and dispersibility.

2 Claims, 4 Drawing Sheets

(56) References Cited

FOREIGN PATENT DOCUMENTS

| | | |
|---|---|---|
| KR | 10-2019-0132113 A | 11/2019 |
| KR | 10-2266386 B1 | 6/2021 |
| KR | 102403554 B1 | 6/2022 |

OTHER PUBLICATIONS

Wang et al, Fabrication and Properties of PLA/nano-HA Composite Scaffolds with Balanced Mechanical Properties and Biological Functions for Bone Tissue Engineering Applications, Nanotechnology Reviews, 10: pp. 1359-1373. (Year: 2021).*

Vaim Co., Ltd., "Study on Improvement of PAL Microparticle Manufacturing Process," Final Report on Product and Process Improvement Technology Development Project, 2015, pp. 1-35.

International Search Report for PCT/KR2023/008194, dated Sep. 12, 2023.

Korean Intellectual Office Communication for KR Application No. 10-2022-0072130, dated Apr. 27, 2023.

Korean Intellectual Office Notice of Preliminary Rejection for 10-2022-0072130, dated Dec. 20, 2022.

Korean Intellectual Office Decision for Grant a Patent for 10-2022-0072130, dated Sep. 20, 2023.

European Patent Office, Communication issued Sep. 23, 2024 in copending European Application No. 23 82 4225.

* cited by examiner

[Fig. 1]
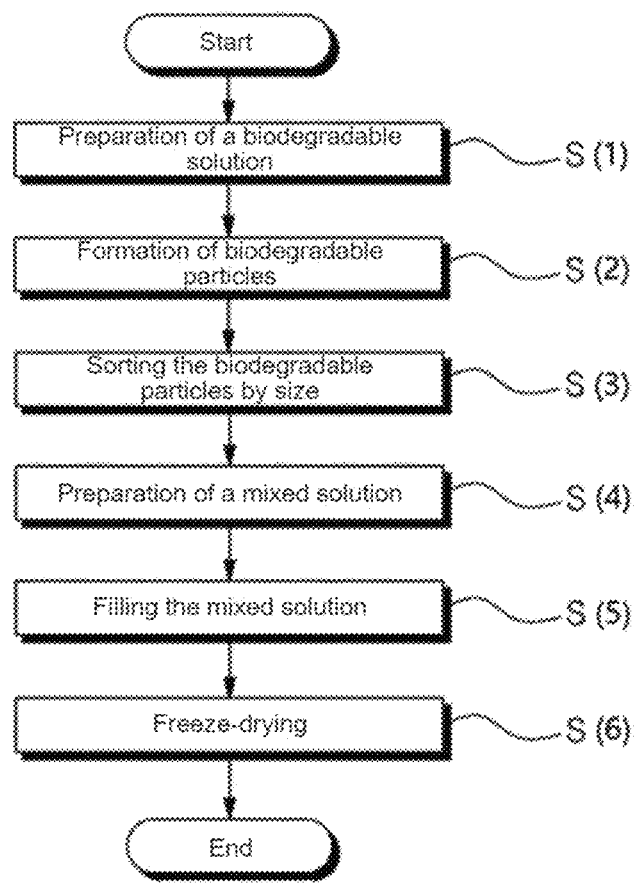

[Fig. 2]
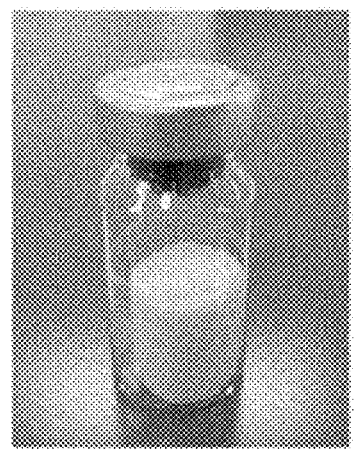
Ex. 1
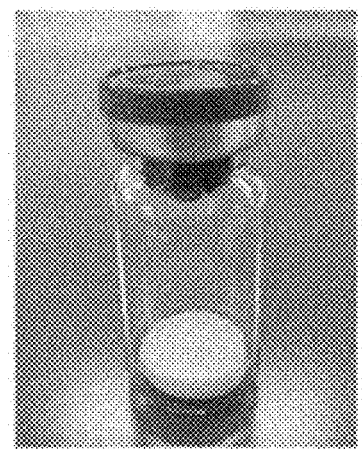
Ex. 5
C. Ex. 1

[Fig. 3]
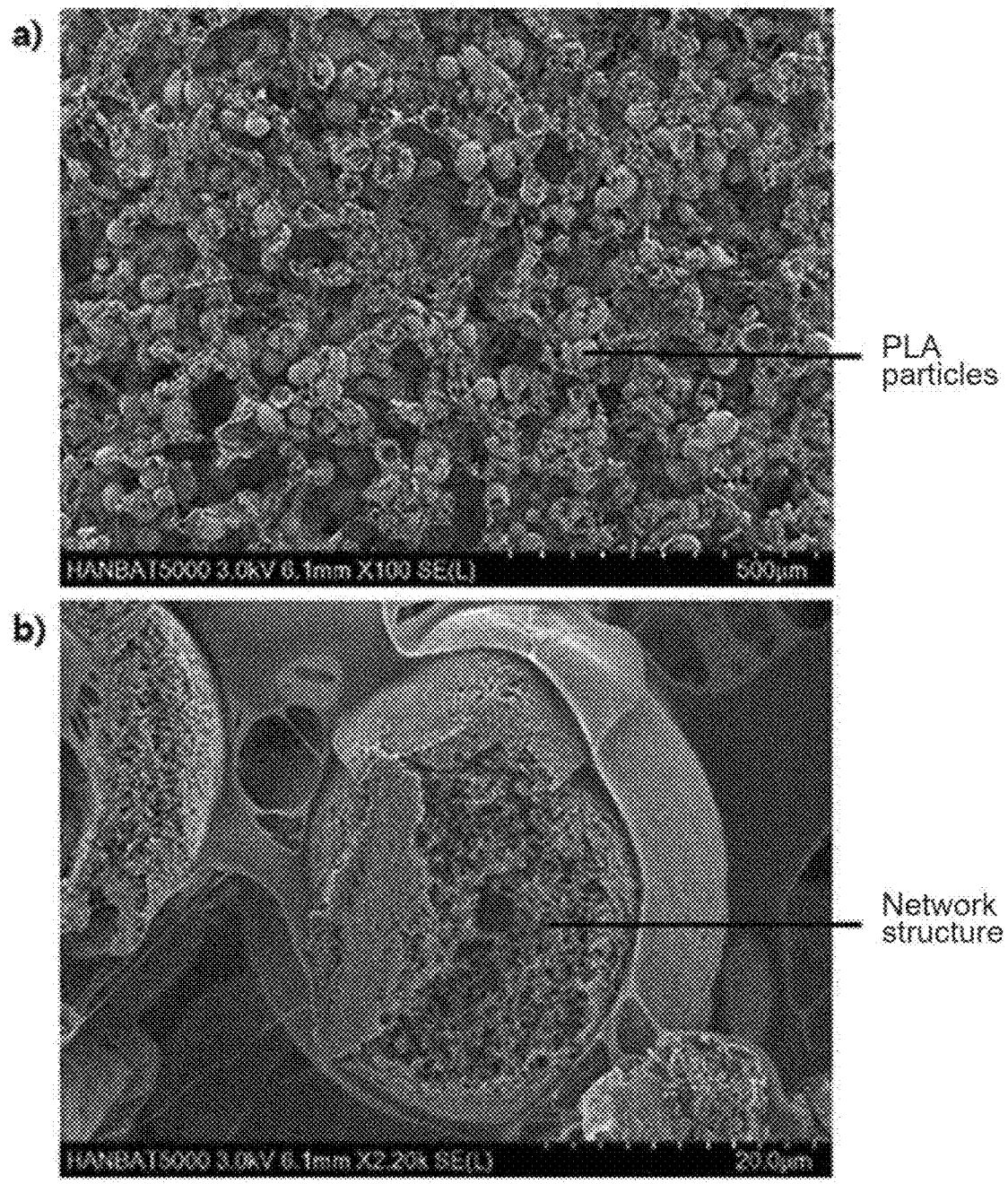

[Fig. 4]
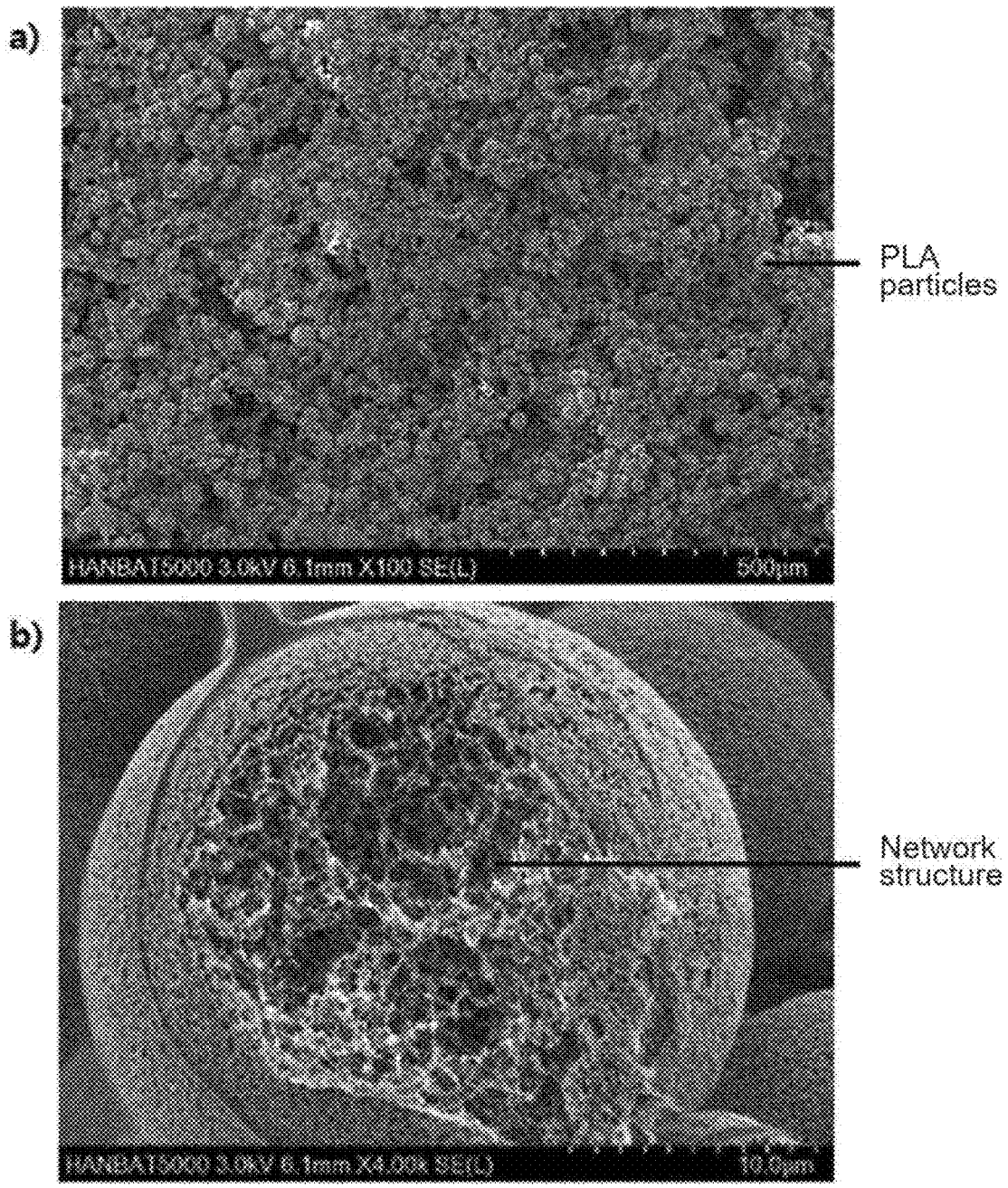

COMPOSITE, MANUFACTURING METHOD THEREFOR, AND COSMETIC SURGERY FILLER COMPOSITION USING SAME

CROSS REFERENCE TO RELATED APPLICATIONS

This application is a National Stage of International Application No. PCT/KR2023/008194 filed Jun. 14, 2023, claiming priority based on Korean Patent Application No. 10-2022-0072130 filed Jun. 14, 2022.

TECHNICAL FIELD

The present invention relates to a composite of two or more components, to a process for preparing the same, and to a filler composition for plastic surgery (e.g., a filler composition for skin plastic surgery) using the same.

BACKGROUND ART

Plastic surgery is being performed to inject filler compositions subcutaneously or into tissues for purposes such as correcting human body functions or cosmetic purposes. Such filler compositions are preferably safe for the human body and biocompatible and biodegradable.

Such filler compositions contain natural polymers such as collagen, gelatin, hyaluronic acid, and dextran, or synthetic polymers such as polylactic acid, polyglutamic acid, polycaprolactone, and polyacrylamide.

However, since the natural polymers or the synthetic polymers begin to decompose after a certain period of time, the shelf life of the filler compositions containing them is limited. In addition, most filler compositions are administered using a syringe. In such an event, if the viscosity of a filler composition is too high or the dispersibility is poor, it may be difficult to inject the filler composition with a thin needle, and the force (injection force) applied to the syringe must increase, causing discomfort and fatigue to the operator.

PRIOR ART DOCUMENTS

Patent Documents (Patent Document 1) Korean Laid-open Patent Publication No. 2017-0123099 (Nov. 7, 2017)

DETAILED DESCRIPTION OF INVENTION

Technical Problem

The present invention aims to provide a composite that has excellent long-term storage and dispersibility and can improve the operating environment of a filler composition for plastic surgery, and a process for preparing the same.

In addition, the present invention aims to provide a filler composition for plastic surgery that can be carried out relatively easily.

Solution to Problem

According to an embodiment of the present invention to accomplish the above object, there is provided a composite that comprises biodegradable particles each having a network structure therein; and a water-soluble polymer, and that has a cake formulation.

According to another embodiment of the present invention, there is provided a process for preparing a composite that comprises (1) dissolving a biodegradable raw material in a first solvent to prepare a biodegradable solution; (2) spraying the biodegradable solution into a second solvent having a lower freezing point than that of the first solvent to form biodegradable particles each having a network structure therein; (3) sorting the biodegradable particles by size; (4) adding the biodegradable particles sorted by size to a water-soluble polymer solution to prepare a mixed solution; (5) filling the mixed solution in a container; and (6) freeze-drying the mixed solution filled in the container to form a composite having a cake formulation.

According to another embodiment of the present invention, there is provided a filler composition for plastic surgery in which the composite is dispersed.

Advantageous Effects of Invention

Since the composite according to the present invention comprises biodegradable particles each having a network structure therein and has a cake formulation with a fluffy texture, it can be dispersed rapidly and uniformly in a solvent. In addition, since the composite according to the present invention has a cake formulation in a solid phase, the decomposition of biodegradable particles and/or water-soluble polymers contained in the composite can be minimized even if it is stored for a long period of time. Accordingly, when the composite according to the present invention is used as a material for a filler composition for plastic surgery, it is possible to extend the shelf life of the material and improve the convenience of storage and handling.

In addition, since the filler composition for plastic surgery according to the present invention is one in which a composite with excellent dispersibility is dispersed, the procedure can be easily performed even if the operator (the person performing the procedure) applies a relatively small force to the syringe.

BRIEF DESCRIPTION OF DRAWINGS

FIG. 1 schematically shows the preparation process of a composite according to an embodiment of the present invention.

FIG. 2 is photographs showing the formulations of the composites according to Example 1, Example 5, and Comparative Example 1 in Test Example 1.

FIG. 3 is an image showing the cross-section of the composite according to Example 1 in Test Example 2 using a scanning electron microscope.

FIG. 4 is an image showing the cross-section of the composite according to Example 5 in Test Example 2 using a scanning electron microscope.

BEST MODE FOR CARRYING OUT THE INVENTION

Hereinafter, the present invention will be described in detail. Here, the present invention is not limited to those described below. Rather, it can be modified into various forms as long as the gist of the invention is not altered.

In the present specification, the term "comprising" is intended to specify a particular characteristic, region, step, process, element, and/or component. It does not exclude the presence or addition of any other characteristic, region, step, process, element and/or component, unless specifically stated to the contrary.

In the present specification, in the case where an element is mentioned to be connected or combined, it means all of the cases where one element is directly, or indirectly through another element, connected or combined with another element.

In the present specification, a singular expression is understood to encompass a singular or plural expression, interpreted in context, unless otherwise specified.

All numbers and expressions related to the quantities of components, reaction conditions, and the like used herein may be modified by the term "about" unless otherwise indicated.

Throughout the description of the embodiments, the terms first, second, and so on are used to describe various components. But the components should not be limited by the terms. The terms are used only for the purpose of distinguishing one component from another.

Composite

The composite according to the present invention may be a composite of materials having biocompatibility and/or biodegradability. Specifically, the composite according to the present invention comprises biodegradable particles each having a network structure therein; and a water-soluble polymer, and it has a cake formulation. Hereinafter, this will be described in detail.

Biodegradable Particles

The biodegradable particles contained in the composite according to the present invention function to restore or replace damaged or aged human tissue (e.g., skin tissue).

The biodegradable particles may be particles each having a network structure therein. Specifically, a three-dimensional network structure that is regular, irregular, or a combination thereof may be formed inside each of the biodegradable particles. As the network structure is present inside each of the biodegradable particles, the biodegradable particles can have high strength, which allows human tissue to be efficiently restored or replaced. In addition, as the biodegradable particles have high strength, the strength of the composite comprising them increases, thereby enhancing the handling convenience of the composite.

The biodegradable particles may comprise a commonly-known biodegradable polymer. Specifically, the biodegradable particles may comprise at least one selected from the group consisting of polylactic acid (PLA), polyglycolic acid (PGA), poly(D,L-lactic acid-co-glycolic acid) (PLGA), polycaprolactone (PCL), polyvalerolactone (PVL), polyhydroxybutyrate (PHB), and polyhydroxyvalerate (PBV), but it is not limited thereto. Preferably, the biodegradable particles may be polylactic acid (PLA) particles.

The biodegradable particles may have a weight average molecular weight of 50,000 to 400,000 g/mole, but it is not limited thereto. Specifically, the weight average molecular weight of the biodegradable particles may be 60,000 to 350,000 g/mole, 70,000 to 300,000 g/mole, 90,000 to 250,000 g/mole, 100,000 to 200,000 g/mole, 130,000 to 190,000 g/mole, or 150,000 to 180,000 g/mole. As the weight average molecular weight of the biodegradable particles is within the above range, processing into a composite is readily carried out, and the dispersibility of the composite can be enhanced.

The biodegradable particles may have a tap density of 0.1 to 0.25 g/ml, but it is not limited thereto. Specifically, the tap density of the biodegradable particles may be 0.1 to 0.24 g/ml, 0.11 to 0.23 g/ml, 0.12 to 0.21 g/ml, 0.13 to 0.18 g/ml, or 0.13 to 0.17 g/ml. As the tap density of the biodegradable particles is within the above range, the biodegradable particles can be densely distributed within the composite, thereby increasing the strength of the composite and enhancing the dispersibility of the composite.

Meanwhile, the biodegradable particles may have a particle size distribution (PSD) of 0.4 to 2.5, 0.5 to 2.2, 0.6 to 2.0, 0.65 to 1.9, 0.7 to 1.8, 0.8 to 1.7, 1.0 to 2.5, 1.0 to 2.3, 1.0 to 2.0, 1.01 to 1.6, 1.02 to 1.5, 1.03 to 1.4, or 1.05 to 1.3 according to the following equation, but it is not limited thereto. As the particle size distribution of the biodegradable particles is within the above range, the dispersibility of the composite in a solvent may be excellent. In addition, when the composite is used as a material for a filler composition for plastic surgery, the injection of the filler composition for plastic surgery can be successfully performed by applying a small force to the syringe even if a thin injection needle is used.

$$PSD = (Dv(90) - Dv(10))/Dv(50) \qquad \text{[Equation 1]}$$

In Equation 1, Dv (10) is the size at which the biodegradable particle distribution is within 10% (the size of the particle at the 10% position based on the volume listed from the smallest particle diameter in a biodegradable particle distribution), Dv (50) is the size at which the biodegradable particle distribution is within 50% (the size of the particle at the 50% position based on the volume listed from the smallest particle diameter in a biodegradable particle distribution), and Dv (90) is the size at which the biodegradable particle distribution is within 90% (the size of the particle at the 90% position based on the volume listed from the smallest particle diameter in a biodegradable particle distribution).

Specifically, in Equation 1, Dv (10) may be 5 to 35 μm, 7 to 33 μm, 10 to 30 μm, 11 to 28 μm, 12 to 25 μm, or 12 to 22 μm, Dv (50) may be 10 to 50 μm, 13 to 47 μm, 15 to 45 μm, 17 to 43 μm, 19 to 42 μm, or 20 to 42 μm, and Dv (90) may be 20 to 90 μm, 25 to 85 μm, 27 to 82 μm, 29 to 80 μm, 30 to 78 μm, or 32 to 75 μm, but they are not limited thereto.

Water-Soluble Polymer

The water-soluble polymer contained in the composite according to the present invention functions as a carrier to transport biodegradable particles and a matrix function to disperse and fix the biodegradable particles.

The water-soluble polymer may comprise a polymer having commonly-known water-solubility properties. Specifically, the water-soluble polymer may comprise at least one selected from the group consisting of hyaluronic acid (HA), methylcellulose (MC), ethylcellulose (EC), carboxymethylcellulose (CMC), hydroxymethylcellulose (HMC), hydroxyethylcellulose (HEC), hydroxypropylcellulose (HPC), hydroxymethyl methacrylate (HEMA), polyvinyl alcohol (PVOH), polyvinylpyrrolidone (PVP), and starch, but it is not limited thereto. Preferably, the water-soluble polymer may be hyaluronic acid (HA). Specifically, the water-soluble polymer may be non-crosslinked hyaluronic acid.

The hyaluronic acid (HA) may be high-molecule hyaluronic acids such as sodium hyaluronate crosspolymer and sodium hyaluronate; medium-molecule hyaluronic acids such as hydroxypropyltrimonium hyaluronate and sodium acetylated hyaluronate; low-molecular hyaluronic acids such as potassium hyaluronate, hydrolyzed hyaluronic acid, and hydrolyzed sodium hyaluronate; ultra-low-molecule hyaluronic acids such as hyaluronic acid; or a combination thereof.

The water-soluble polymer may have a weight average molecular weight of 1,000,000 to 4,000,000 g/mole, but it is not limited thereto. Specifically, the weight average molecular weight of the water-soluble polymer may be 1,200,000 to 4,000,000 g/mole, 1,300,000 to 4,000,000 g/mole, 1,500,000 to 4,000,000 g/mole, 1,800,000 to 4,000,000 g/mole, 2,000,000 to 4,000,000 g/mole, 2,100,000 to 3,800,000 g/mole, or 2,200,000 to 3,600,000 g/mole. As the weight average molecular weight of the water-soluble polymer is within the above range, processing into a composite is readily carried out, and the dispersibility of the composite can be enhanced.

According to the present invention, the weight ratio of the biodegradable particles to the water-soluble polymer may be 40:60 to 95:5, but it is not limited thereto. Specifically, the weight ratio of the biodegradable particles and the water-soluble polymer contained in the composite may be 45:55 to 95:5, 45:55 to 90:10, 50:50 to 90:10, 55:45 to 85:15, 60:40 to 85:15, 65:35 to 85:15, 70:30 to 85:15, 75:25 to 85:15, 80:20 to 85:15, or 70:30 to 80:20. As the weight ratio is within the above range, the dispersibility of the composite is excellent, and the composite can be efficiently used as a material for a filler composition for plastic surgery.

Meanwhile, the composite according to the present invention may have a compressive strength of 0.02 to 1.5 MPa, but it is not limited thereto. Specifically, the compressive strength of the composite according to the present invention may be 0.025 to 1.3 MPa, 0.03 to 1.2 MPa, 0.033 to 1.0 MPa, 0.035 to 1.0 MPa, 0.035 to 0.8 MPa, 0.035 to 0.6 MPa, 0.036 to 0.5 MPa, 0.036 to 0.45 MPa, 0.036 to 0.43 MPa, 0.037 to 0.4 MPa, 0.037 to 0.39 MPa, 0.037 to 0.38 MPa, or 0.037 to 0.37 MPa.

In addition, the composite according to the present invention may have an apparent volume of 10 to 40 ml/g, but it is not limited thereto. Specifically, the apparent volume of the composite according to the present invention may be 10 to 35 ml/g, 10 to 32 ml/g, 10 to 30 ml/g, 12 to 29 ml/g, 14 to 29 ml/g, 15 to 28 ml/g, 15.5 to 28 ml/g, or 16 to 28 ml/g.

In addition, the composite according to the present invention may have a porosity of 90 to 97.5% by volume, but it is not limited thereto. Specifically, the porosity of the composite according to the present invention may be 90 to 97% by volume, 90 to 96% by volume, or 90 to 95% by volume. The porosity may refer to the volume of pores present in the composite out of the total volume of the composite.

As the composite according to the present invention has compressive strength, apparent density, and porosity within the above specific ranges, it may have excellent long-term storage, handling convenience, and dispersibility. In particular, since the compressive strength of the composite according to the present invention is adjusted to the specific range, when the composite is dispersed in a solvent for preparing a filler composition for plastic surgery, it can be uniformly dispersed within a short period of time.

Specifically, the suspension time of the composite according to the present invention in an aqueous solvent may be 30 minutes or less, but it is not limited thereto. More specifically, the suspension time of the composite according to the present invention in an aqueous solvent may be 1 to 30 minutes, 5 to 30 minutes, 10 to 30 minutes, 10 to 29 minutes, 10 to 25 minutes, 10 to 20 minutes, or 12 to 19 minutes. Here, the aqueous solvent may specifically be water, distilled water, deionized water, ultrapure water, or the like, but it is not limited thereto.

The composite according to the invention may be in the form of a cake formulation with a fluffy texture. As the composite has a cake formulation, it can have excellent long-term storage and dispersibility in a solvent.

Specifically, the composite according to the present invention may have a cylindrical shape, but it is not limited thereto. In addition, the composite may have an average diameter of 1 to 5 cm, 1 to 3 cm, 1 to 2.5 cm, 1.2 to 2.2 cm, or 1.5 to 2.0 cm, and an average height of 0.2 to 5 cm, 0.3 to 3 cm, 0.5 to 3 cm, or 0.5 to 2.5 cm, but they are not limited thereto.

Process for Preparing a Composite

The present invention may provide a process for preparing the above composite. Specifically, the process for preparing a composite according to the present invention comprises (1) dissolving a biodegradable raw material in a first solvent to prepare a biodegradable solution; (2) spraying the biodegradable solution into a second solvent having a lower freezing point than that of the first solvent to form biodegradable particles each having a network structure therein; (3) sorting the biodegradable particles by size; (4) adding the biodegradable particles sorted by size to a water-soluble polymer solution to prepare a mixed solution; (5) filling the mixed solution in a container; and (6) freeze-drying the mixed solution filled in the container to form a composite having a cake formulation.

Step (1) is to dissolve a biodegradable raw material in a first solvent to prepare a biodegradable solution. Specifically, step (1) may be carried out by adding the biodegradable raw material to a first solvent in which two or more organic solvents are mixed and stirring it.

Specifically, the biodegradable raw material may comprise at least one selected from the group consisting of polylactic acid (PLA), polyglycolic acid (PGA), poly(D,L-lactic acid-co-glycolic acid) (PLGA), polycaprolactone (PCL), polyvalerolactone (PVL), polyhydroxybutyrate (PHB), and polyhydroxyvalerate (PBV), but it is not limited thereto.

The biodegradable raw material may have a weight average molecular weight of 50,000 to 400,000 g/mole, but it is not limited thereto. Specifically, the weight average molecular weight of the biodegradable raw material may be 60,000 to 350,000 g/mole, 70,000 to 300,000 g/mole, 90,000 to 250,000 g/mole, 100,000 to 200,000 g/mole, 130,000 to 190,000 g/mole, or 150,000 to 180,000 g/mole.

The first solvent may specifically be at least two selected from the group consisting of dimethyl sulfoxide, diethyl sulfoxide, ethylene carbonate, propylene carbonate, dimethyl carbonate, N-methyl-2-pyrrolidone, N-ethyl-2-pyrrolidone, N-hydroxyethyl-2-pyrrolidone, N-cyclohexyl-2-pyrrolidone, N-methylformamide, N,N-dimethylformamide, N-ethylformamide, N,N-ethylformamide, N-methylacetamide, N,N-dimethylacetamide, N,N-diethylacetamide, isopropyl acetate, ethyl acetate, methyl acetate, dimethyl ketone, diethyl ketone, methyl ethyl ketone, isopropyl ketone, methyl propyl ketone, methyl butyl ketone, methyl isobutyl ketone, and tetrahydrofuran, but it is not limited thereto.

Specifically, the first solvent may be a solvent in which a first organic solvent and a second organic solvent are mixed at a weight ratio of 70:30 to 98:2, 75:25 to 98:2, 80:20 to 95:5, 85:15 to 95:5, or 85:15 to 90:10. More specifically, the first solvent may be a mixed solvent of dimethyl sulfoxide and ethylene carbonate, but it is not limited thereto.

Step (2) is to spray the biodegradable solution into a second solvent having a lower freezing point than that of the first solvent to form biodegradable particles each having a network structure therein. Specifically, step (2) may be carried out by spraying the biodegradable solution into a second solvent that does not mix with the first solvent to be separated in phase and has a freezing point that is lower than the freezing point of the first solvent by 50 to 150° C. (specifically, 90 to 120° C.).

The temperature of the second solvent during the spraying may be specifically −45 to 0° C., −40 to −5° C., −35 to −10° C., or −30 to −10° C., but it is not limited thereto. As the temperature of the second solvent is within the above range, biodegradable particles having a desired particle size distribution and a network structure therein can be well formed.

The second solvent may be at least one selected from the group consisting of pentane, hexane, heptane, octane, nonane, and decane, but it is not limited thereto.

The spraying speed of the biodegradable solution sprayed into the second solvent may be 1 to 20 ml/minute, 3 to 15 ml/minute, or 5 to 10 ml/minute, but it is not limited thereto.

Step (3) is to sort the biodegradable particles by size. Specifically, step (3) may be carried out by feeding the biodegradable particles into a particle sorter to select particles having the required size.

The size of the biodegradable particles selected through the particle sorter is not particularly limited, but the size may be such that Dv (50) (average particle diameter) is 10 to 60 μm (specifically, 13 to 47 μm or 15 to 45 μm). The particle size distribution of the biodegradable particles can be adjusted to a specific range through this step. When the composite is prepared using the biodegradable particles with a controlled particle size distribution, it is possible to provide a composite with excellent dispersibility in a solvent.

Step (4) is to add the biodegradable particles sorted by size to a water-soluble polymer solution to prepare a mixed solution. Specifically, step (4) may be carried out by adding the biodegradable particles sorted by size to a solution with a controlled concentration of the water-soluble polymer and stirring it.

The water-soluble polymer contained in the water-soluble polymer solution may specifically comprise at least one selected from the group consisting of hyaluronic acid (HA), methylcellulose (MC), ethylcellulose (EC), carboxymethylcellulose (CMC), hydroxymethylcellulose (HMC), hydroxyethylcellulose (HEC), hydroxypropylcellulose (HPC), hydroxymethyl methacrylate (HEMA), polyvinyl alcohol (PVOH), polyvinylpyrrolidone (PVP), and starch, but it is not limited thereto.

The water-soluble polymer may have a weight average molecular weight of 1,000,000 to 4,000,000 g/mole, but it is not limited thereto. Specifically, the weight average molecular weight of the water-soluble polymer may be 1,200,000 to 4,000,000 g/mole, 1,300,000 to 4,000,000 g/mole, 1,500,000 to 4,000,000 g/mole, 1,800,000 to 4,000,000 g/mole, 2,000,000 to 4,000,000 g/mole, 2,100,000 to 3,800,000 g/mole, or 2,200,000 to 3,600,000 g/mole.

The content of the water-soluble polymer contained in the water-soluble polymer solution may be 0.2 to 2% by weight, 0.4 to 1.5% by weight, 0.5 to 1.3% by weight, 0.5 to less than 1% by weight, or 0.6 to 0.95% by weight, based on the total weight of the water-soluble polymer solution, but it is not limited thereto. As the content of the water-soluble polymer is within the above range, the strength of the composite can be secured while the dispersibility of the composite in a solvent can be increased.

The solvent contained in the water-soluble polymer solution may be a commonly known aqueous solvent (e.g., water, distilled water, or the like).

Meanwhile, the water-soluble polymer solution and the biodegradable particles may be mixed such that the weight ratio (a:b) of the water-soluble polymer (a) contained in the water-soluble polymer solution to the biodegradable particles (b) is 40:60 to 95:5, 45:55 to 95:5, 45:55 to 90:10, 50:50 to 90:10, 55:45 to 85:15, 60:40 to 85:15, 65:35 to 85:15, 70:30 to 85:15, 75:25 to 85:15, 80:20 to 85:15, or 70:30 to 80:20.

Step (5) is to fill the mixed solution in a container. Specifically, step (5) may be carried out by filling the mixed solution in a specific container to form a composite having a cake formulation.

The container may specifically be a sealable glass bottle (e.g., a vial), but it is not limited thereto.

The amount of the mixed solution filled in the container may be 10 to 80% by volume, 15 to 70% by volume, 15 to 65% by volume, 20 to 60% by volume, or 25 to 55% by volume, based on the total volume of the container, but it is not limited thereto. As the filling amount of the mixed solution is within the above range, it is possible to form a composite in a cake formulation having the required compressive strength.

Step (6) is to freeze-dry the mixed solution filled in the container to form a composite having a cake formulation. Specifically, step (6) may comprise (6-1) freezing the mixed solution at −60 to −10° C. to obtain a frozen product; (6-2) first heating the frozen product to a temperature of −5 to 5° C. for 1 to 3 hours in a vacuum atmosphere; (6-3) second heating the frozen product, first heated, to a temperature of 20 to 25° C. for 8 to 15 hours in a vacuum atmosphere; and (6-4) drying the frozen product, second heated, at a temperature of 25° C. or higher for 20 to 40 hours in a vacuum atmosphere.

The temperature for freezing the mixed solution in step (6-1) may be −60 to −10° C., −50 to −20° C., or −40 to −30° C., but it is not limited thereto. In addition, the time for freezing the mixed solution may be 60 to 240 minutes, 90 to 180 minutes, or 120 to 150 minutes, but it is not limited thereto.

Steps (6-2) to (6-4) are to dry (evaporate) the solvent present in the frozen product by gradually raising the temperature of the frozen product. In such an event, the final degree of vacuum in each step may be 0.1 to 30 mTorr, 0.5 to 20 mTorr, or 1 to 10 mTorr, but it is not limited thereto.

Specifically, step (6-2) may be carried out by first raising the temperature of the frozen product, which is −60 to −10° C., to a temperature of −5 to 5° C., −3 to 3° C., or −1 to 1° C. over 1 to 3 hours or 1.5 to 2.5 hours in a vacuum atmosphere.

Step (6-3) may be carried out by second raising the first-raised temperature of the frozen product to a temperature of 20 to 25° C., 22 to 25° C., or 24 to 25° C. over 8 to 15 hours or 9 to 11 hours in a vacuum atmosphere.

Step (6-4) may be carried out by raising the temperature of the second-raised frozen product to a temperature of 25° C. or higher (specifically 25 to 30° C.) over 20 to 40 hours or 22 to 30 hours in a vacuum atmosphere to finally dry it.

As the freeze-drying of the mixed solution is carried out through steps (6-1) to (6-4), a composite having a cake formulation can be efficiently formed.

Meanwhile, the process for preparing a composite according to the present invention may further comprise sterilizing the composite.

The sterilization may be carried out by gamma ray sterilization, e-beam sterilization, ethylene oxide sterilization, steam sterilization, or high-pressure steam sterilization, but it is not limited thereto. Specifically, the sterilization may be carried out using ethylene oxide at 30 to 40° C. for 150 to 180 minutes. This procedure can further enhance the long-term storage of the composite.

The size of the biodegradable particles contained in the composite prepared through the above preparation process is not particularly limited, but the average particle diameter (Dv (50)) may be 15 to 60 μm. Specifically, the biodegradable particles may be first biodegradable particles having a Dv (50) particle size distribution of 15 to 30 µm, 17 to 29 µm, 18 to 28 µm, 19 to 27 µm, 20 to 25 µm, or 21 to 23 µm; second biodegradable particles having a Dv (50) particle size distribution of greater than 30 to 60 µm, greater than 30 to 55 µm, 35 to 50 µm, 35 to 48 µm, 38 to 45 µm, or 40 to 43 µm; or a mixture thereof, but they are not limited thereto.

Specifically, the biodegradable particles contained in the composite prepared through the above preparation process may have a particle size distribution (PSD) of 0.4 to 2.5, 0.5 to 2.2, 0.6 to 2.0, 0.65 to 1.9, 0.7 to 1.8, 0.8 to 1.7, 1.0 to 2.5, 1.0 to 2.3, 1.0 to 2.0, 1.01 to 1.6, 1.02 to 1.5, 1.03 to 1.4, or 1.05 to 1.3 according to the following equation, but it is not limited thereto.

$$PSD = (Dv(90) - Dv(10))/Dv(50) \quad \text{[Equation 1]}$$

In Equation 1, Dv (10) is the size at which the biodegradable particle distribution is within 10%, Dv (50) is the size at which the biodegradable particle distribution is within 50%, and Dv (90) is the size at which the biodegradable particle distribution is within 90%.

In the present invention, a composite is prepared by filling a mixed solution obtained by mixing biodegradable particles with a specific particle size distribution and a water-soluble polymer solution in a sealable container and freeze-drying the same; thus, it is possible to obtain a composite with a specific cake formulation and controlled compressive strength.

As the composite according to the present invention has a cake formulation, it has excellent long-term storage and dispersibility and enhanced handling convenience by virtue of controlled compressive strength. In addition, as the composite according to the present invention comprises biodegradable particles and a water-soluble polymer, it can have biocompatibility and biodegradability.

Accordingly, the composite according to the present invention can be advantageously used as a material to restore or replace human tissue. In addition, the composite according to the present invention can be used as a carrier for cells or drugs, a culture medium for cells, or the like.

Filler Composition for Plastic Surgery

The present invention provides a filler composition for plastic surgery in which the above composite is dispersed. Specifically, the filler composition for plastic surgery according to the present invention may be one in which a composite having the same composition and characteristics as described above is dispersed in a solvent.

The filler composition for plastic surgery according to the present invention can be prepared within a short period of time (e.g., within 30 minutes) by virtue of the enhanced dispersibility of the composite. That is, as a sealed composite having a cake formulation in a solid phase is used, solubility and dispersibility are enhanced, making it possible to prepare a filler composition for plastic surgery within a short period of time. Thus, it is possible in the present invention to readily prepare a filler composition for plastic surgery immediately before the procedure. In addition, since the composite comprises biodegradable particles with a controlled particle size distribution, the filler composition for plastic surgery of the present invention obtained by dispersing it in a solvent allows the operator to easily perform the procedure while applying a small force to the syringe even when a needle with a thin diameter is used. Thus, the filler composition for plastic surgery according to the present invention can reduce operator discomfort and fatigue while improving the operating environment.

For example, the filler composition for plastic surgery according to the present invention (e.g., a composition in which a composite having an average particle diameter (Dv (50)) of 60 µm or less is dispersed) may have an injection force of 2.0 N or less for an injection needle having a gauge (G) of 26, specifically, 0.3 to 1.5 N, 0.5 to 1.3 N, 0.7 to 1.25 N, or 0.9 to 1.20 N, but it is not limited thereto. In addition, the filler composition for plastic surgery according to the present invention (e.g., a composition in which a composite having an average particle diameter (Dv (50)) of 33 µm or less is dispersed) may have an injection force of 3.0 N or less for an injection needle having a gauge (G) of 30, specifically, 1.6 to 2.6 N, 1.7 to 2.4 N, 1.8 to 2.2 N, or 1.9 to 2.0 N, but it is not limited thereto.

MODE FOR THE INVENTION

Hereinafter, the present invention will be described in detail with reference to examples. But the scope of the present invention is not limited to the Examples.

Example 1

9 g of a polylactic acid (PLA) with a weight average molecular weight of 170,000 g/mole was dissolved in 150 ml of a mixed solvent of dimethyl sulfoxide and ethylene carbonate at a weight ratio of 90:10 to produce a polylactic acid solution.

Next, the polylactic acid solution thus prepared was sprayed into n-hexane cooled to −20° C. or lower at a spray rate of 4.5 ml/minute and a spray air volume of 6 liters/minute to form frozen polylactic acid particles in n-hexane. The frozen polylactic acid particles thus formed were obtained, added into water at 1 to 3° C., and stirred to remove the mixed solvent (dimethyl sulfoxide and ethylene carbonate) contained in the frozen polylactic acid particles, thereby preparing polylactic acid particles (PLA particles).

Subsequently, the polylactic acid particles thus prepared were sorted using a particle sorter to obtain polylactic acid particles with a particle diameter of 60 µm or less (Dv (50): 41.9 µm).

Next, the polylactic acid particles with a particle diameter of 60 µm or less were added to a sodium hyaluronate solution having a concentration of 0.6% (HA solution=99.4% by weight of distilled water+0.6% by weight of sodium hyaluronate) such that the weight ratio of the polylactic acid particles to the sodium hyaluronate (HA) was 85:15, followed by mixing thereof to prepare a mixed solution.

Next, 5.20 g of the mixed solution (170 mg of PLA particles and 30 mg of HA) thus prepared was filled in a 10-ml vial.

Next, the mixed solution filled in the vial was frozen at −40 to −30° C. to obtain a frozen product. The temperature of the frozen product thus obtained was first raised from −30° C. to 0° C. over 2 hours in a vacuum atmosphere, the temperature was then raised again from 0° C. to 25° C. over 10 hours, and it was then dried at 25° C. for 24 hours to form a composite in the vial.

Thereafter, the vial containing the composite was sterilized using ethylene oxide (EO) gas, and residual moisture was removed through vacuum drying to prepare a composite with a diameter of 1.8 cm and a height of 2.2 cm in the vial.

Examples 2 to 4

Each composite was prepared through the same procedure as in Example 1, except that the concentration of sodium hyaluronate (HA) contained in the mixed solution filled in a vial, the amount of mixed solution filled, and the diameter and height of the composite were adjusted as shown in Table 1 below.

TABLE 1

| PLA/HA concentration | Filling amount of the mixed solution (g) | Weight ratio of PLA:HA = 85:15 | | Composite diameter (cm) | Composite height (cm) |
|---|---|---|---|---|---|
| | | PLA (mg) | HA (mg) | | |
| Ex. 1 HA concentration: 0.6% PLA concentration: 3.4% | 5.20 | 170 | 30 | 1.8 | 2.2 |
| Ex. 2 HA concentration: 0.8% PLA concentration: 4.5% | 3.95 | 170 | 30 | 1.8 | 1.5 |
| Ex. 3 HA concentration: 1.0% PLA concentration: 5.7% | 3.20 | 170 | 30 | 1.8 | 1.2 |
| Ex. 4 HA concentration: 1.2% PLA concentration: 6.8% | 2.70 | 170 | 30 | 1.8 | 0.8 |

Example 5

A composite with a diameter of 1.8 cm and a height of 0.55 cm was prepared through the same procedure as in Example 1, except that the polylactic acid particles were sorted using a particle sorter to obtain polylactic acid particles with a particle diameter of 33 μm or less (Dv (50): 21.1 μm), which were added to the sodium hyaluronate solution.

Comparative Example 1

A composite with a diameter of 1.8 cm was prepared through the same procedure as in Example 1, except that the mixed solution (170 mg of PLA particles and 30 mg of HA) was filled in a vial and was vacuum-dried at 25° C. for 16 hours in a vacuum atmosphere (i.e., no freeze-drying and sterilization steps were performed).

Test Example 1: Observation of Formulation

The formulations of the composites prepared in Examples 1, 5, and Comparative Example 1 were visually observed. The results are shown in FIG. 2.

Referring to FIG. 2, the composites of Examples 1 and 5 had a cake formulation (cylindrical shape). In contrast, the composite of Comparative Example 1 did not have a regular shape since the mixed solution swelled during the vacuum drying process.

Here, as the composites in Examples 1 and 5 had a cake formulation, the present invention can increase the dispersibility and use convenience of the composite. This can be confirmed in Test Examples 7 and 8 below.

Test Example 2: Observation of the Internal Structure of Polylactic Acid Particles and the Structure of Composite The composites prepared in each of Examples 1 and 5 were cut in the vertical direction, and the cross sections were observed using a scanning electron microscope (manufacturer: Hitachi High Technology, model name: Hitachi su5000). The results are shown in FIGS. 3 and 4.

Referring to a) each shown in FIGS. 3 and 4, in the composites of Examples 1 and 5, polylactic acid particles each maintaining its shape were uniformly present inside the composite.

In addition, referring to b) each shown in FIGS. 3 and 4, the polylactic acid particles present in the composites of Examples 1 and 5 each had a network structure therein.

Test Example 3: Measurement of Tap Density

The polylactic acid (PLA) particles obtained through the process of sorting with a particle sorter in each of Examples 1 and 5 were measured for tap density according to the following measurement method. The results are shown in Table 2 below.

*Method for Measuring Tap Density
1) The weight of a measuring cylinder was measured, and 20 to 25 ml of polylactic acid particles was placed in the measuring cylinder.
2) The weight of the measuring cylinder containing the polylactic acid particles was measured to calculate the weight of the polylactic acid particles only.
3) The measuring cylinder containing the polylactic acid particles was mounted on a tap density meter (manufacturer: Bettersize, model name: BeDensi T1 Pro).
4) The tap density meter was operated under the conditions of a tapping speed of 250 times/minute and a tapping count of 1,250 times.
5) Upon completion of the tapping, the measuring cylinder was taken out, and the volume of the polylactic acid particles was measured.
6) The weight of the polylactic acid particles measured in step 2) was divided by the volume of the polylactic acid particles measured in step 5) to calculate the tap density (measure tap density for each of 5 samples and obtain the average value).

TABLE 2

| Sample | PLA particle size | Weight (g) | Volume (ml) | Tap density (g/ml) | Avg. tap density (g/ml) |
|---|---|---|---|---|---|
| 1 | 33 μm or less | 3.1 | 19.4 | 0.160 | 0.165 |
| 2 | (Example 5) | 3.0 | 17.6 | 0.170 | |
| 3 | | 3.2 | 18.1 | 0.177 | |
| 4 | | 3.2 | 19.8 | 0.162 | |
| 5 | | 3.1 | 19.8 | 0.157 | |
| 1 | 60 μm or less | 2.0 | 14.8 | 0.135 | 0.138 |
| 2 | (Example 1) | 2.9 | 19.8 | 0.146 | |
| 3 | | 3.0 | 20.8 | 0.144 | |

TABLE 2-continued

| Sample | PLA particle size | Weight (g) | Volume (ml) | Tap density (g/ml) | Avg. tap density (g/ml) |
|---|---|---|---|---|---|
| 4 | | 2.9 | 22.0 | 0.132 | |
| 5 | | 2.4 | 18.0 | 0.133 | |

Referring to Table 2 above, the polylactic acid particles prepared in each of Examples 1 and 5 had a tap density in the range of 0.1 to 0.2 g/ml. Here, in Example 5, where the particle size of the polylactic acid particles was smaller than that of Example 1, the tap density of the polylactic acid particles was larger. Thus, it is expected that bonding in high density within the composite would be achieved.

Test Example 4: Measurement of Particle Size Distribution

The polylactic acid particles prepared in each of Examples 1 and 5 were measured for particle size distribution according to the following measurement method. The results are shown in Table 3 below.
*Method for Measuring Particle Size Distribution
1) The composite were added to water and stirred for 30 minutes to prepare a suspension.
2) The prepared suspension was analyzed with a particle size distribution meter (manufacturer: Malvern Instrument, model name: Mastersizer 3000-Maz6140) to measure the particle size distribution of the polylactic acid particles.
3) The particle size distribution (PSD) was calculated from the values measured in step 2) using the following Equation 1.

$$PSD = (Dv(90) - Dv(10))/Dv(50) \quad \text{[Equation 1]}$$

In Equation 1, Dv (10) is the size at which the biodegradable particle distribution is within 10%, Dv (50) is the size at which the biodegradable particle distribution is within 50%, and Dv (90) is the size at which the biodegradable particle distribution is within 90%.

TABLE 3

| | Dv (10) | Dv (50) | Dv (90) | Particle size distribution |
|---|---|---|---|---|
| Ex. 1 | 20.9 μm | 41.9 μm | 73.9 μm | 1.265 |
| Ex. 5 | 11.6 μm | 21.1 μm | 34.4 μm | 1.081 |

Referring to Table 3 above, the polylactic acid particles prepared in each of Examples 1 and 5 had a particle size distribution in the range of 1.0 to 2.5. Here, as the particle size distribution of polylactic acid particles was within the above range, the present invention could increase the use convenience (utility) of the composite. That is, with a particle size distribution within the above range, the dispersibility of the composite is excellent, and the suspension is discharged smoothly even when a relatively small force (injection force) is applied to the syringe filled with the suspension in which the composite is dispersed. This can be confirmed in Test Examples 7 and 8 below.

Test Example 5: Measurement of Compressive Strength

The composite prepared in each of Examples 1 to 4 and Comparative Example 1 was measured for compressive strength using an Instron 5848 (model name) instrument (measurement conditions–compression speed: 10 mm/minute, maximum compression ratio: 75%). The results are shown in Table 4 below.

TABLE 4

| | HA concentration (%) | Compressive strength (MPa) |
|---|---|---|
| Ex. 1 | 0.6 | 0.03750 |
| Ex. 2 | 0.8 | 0.36316 |
| Ex. 3 | 1.0 | 0.50605 |
| Ex. 4 | 1.2 | 0.94671 |
| C. Ex. 1 | 0.6 | Not measurable (irregular shape) |

Referring to Table 4 above, the composites in each of Examples 1 to 4 had a compressive strength in the range of 0.03 to 1 MPa. Further, it is understood that the concentration of sodium hyaluronate (HA) has an impact on the compressive strength of the composite.

Meanwhile, since the composite of Comparative Example 1 had an irregular shape, the compressive strength could not be measured.

Test Example 6: Measurement of Apparent Volume

The composite prepared in each of Examples 1 to 4 and Comparative Example 1 was measured for apparent volume using the diameter and height of the composite. The results are shown in Table 5 below.

TABLE 5

| | HA concentration (%) | Apparent volume (ml/g) |
|---|---|---|
| Ex. 1 | 0.6 | 27.9 |
| Ex. 2 | 0.8 | 17.0 |
| Ex. 3 | 1.0 | 15.2 |
| Ex. 4 | 1.2 | 10.1 |
| C. Ex. 1 | 0.6 | Not measurable (irregular shape) |

Referring to Table 5 above, the composites in each of Examples 1 to 4 had an apparent volume in the range of 10 to 40 ml/g. Further, it is understood that in order to increase the porosity of the composite, it is desirable to lower the concentration of sodium hyaluronate (HA). Here, if the composite has high porosity, it can be suspended rapidly in an aqueous solvent for use, thereby increasing the use convenience of the composite. This can be confirmed in Test Examples 7 and 8 below.

Meanwhile, since the composite of Comparative Example 1 had an irregular shape, the apparent volume could not be measured.

Test Example 7: Measurement of Suspension Time

The composite prepared in each of Examples 1 to 4 and Comparative Example 1 was measured for suspension time according to the following measurement method. The results are shown in Table 6 below.

*Method for Measuring Suspension Time
1) 8 ml of distilled water was added to a vial containing the composite, which was left for about 5 minutes.
2) The vial was stirred for 5 minutes with the rpm of a vortex mixer set to 3,000.
3) Whether the composite in the vial had been completely dissolved and granulated was visually checked.
4) The procedure in step 2) was repeated until the composite was completely dissolved, and the time taken for being granulated was measured.

TABLE 6

| | HA concentration (%) | Sample | rpm | Suspension time (min) | Avg. suspension time (min) |
|---|---|---|---|---|---|
| Ex. 1 | 0.6 | 1 | 3,000 | 15 | 15.0 |
| | | 2 | | 15 | |
| | | 3 | | 15 | |
| Ex. 2 | 0.8 | 1 | 3,000 | 20 | 18.3 |
| | | 2 | | 15 | |
| | | 3 | | 20 | |
| Ex. 3 | 1.0 | 1 | 3,000 | 25 | 26.6 |
| | | 2 | | 25 | |
| | | 3 | | 30 | |
| Ex. 4 | 1.2 | 1 | 3,000 | 25 | 28.3 |
| | | 2 | | 30 | |
| | | 3 | | 30 | |

Referring to Table 6 above, the composite in each of Examples 1 to 4 was rapidly suspended (dispersed) with a suspension time of 30 minutes or less. As the suspension is accomplished in a short period of time, the composite according to the present invention has excellent use convenience. For example, when the composite is suspended in an aqueous solvent at the treatment site for skin treatment, it can be suspended within a short period of time, increasing treatment efficiency.

Here, the suspension of the composite according to the present invention is possible in a short period of time since the composite has a cake formulation and has particle size distribution, compressive strength, and apparent volume within specific ranges. This supports the importance of controlling the shape, compressive strength, apparent volume, and particle size distribution of polylactic acid particles of the composite.

Further, it was confirmed that the lower the concentration of sodium hyaluronate (HA), the shorter the suspension time. Thus, in order to increase the use convenience of the composite, it is desirable to control the concentration of hyaluronic acid, which forms the support structure (frame) of the composite.

Test Example 8: Measurement of Injection Force

The composite prepared in each of Examples 1 and 5 was measured for injection force according to the following measurement method. The results are shown in Table 7 below.
*Method for Measuring Injection Force
1) 5 ml of distilled water was added to a vial containing the composite and stirred with a vortex mixer until the composite was dissolved and granulated (suspension preparation).
2) 0.5 to 0.6 ml of the suspension in the vial was charged to a 1-ml disposable syringe.
3) A 26 G or 30 G injection needle was assembled to the syringe, and the syringe was fixed into the support of a universal testing machine (manufacturer: TestOne, model name: TO-102) with the needle facing downward.
4) The universal testing machine was operated to press the push bar attached to the injection tube at 1 mm/sec until the injection tube was completely empty, and the measured force was recorded.
5) In the graph recording the measured force, calculate the average value (input force) of the forces measured at a point 5 mm to the right of the starting point, at a point 5 mm to the left of the ending point, and the midpoint between these two points.

TABLE 7

| | Needle gauge (G) | Injection force (N) |
|---|---|---|
| Ex. 1 | 26 | 1.12 |
| Ex. 5 | 26 | 0.80 |
| | 30 | 1.80 |

Referring to Table 7 above, the composites of Examples 1 and 5 had a low injection force; thus, the suspension in which the composite was dispersed was smoothly discharged from the syringe even when a relatively small force was applied. As the injection force is small, the composite according to the present invention has excellent use convenience. For example, when a suspension in which the composite is dispersed is used at the treatment site, the suspension is smoothly discharged from the syringe and injected into the skin even if a relatively small force is applied to the syringe. Thus, the convenience of the procedure can be enhanced.

This result also supports the importance of controlling the shape, compressive strength, apparent volume, and particle size distribution of polylactic acid particles of the composite.

The invention claimed is:
1. A composite, which comprises biodegradable particles each having a network structure therein; and a water-soluble polymer,
   wherein the weight ratio of the biodegradable particles to the water-soluble polymer is 60:40 to 85:15,
   wherein the biodegradable particles comprise polylactic acid (PLA),
   wherein the water-soluble polymer comprises hyaluronic acid (HA), and
   wherein the composite has a compressive strength of 0.037 to 0.37 MPa, an apparent volume of 17 to 40 ml/g, and a tap density of 0.1 to 0.25 g/ml.

2. The composite of claim 1, wherein the suspension time of the composite in an aqueous solvent is 30 minutes or less.

\* \* \* \* \*